US009202293B2

(12) United States Patent
Iida et al.

(10) Patent No.: US 9,202,293 B2
(45) Date of Patent: Dec. 1, 2015

(54) METHOD OF EXTRACTING CONTOUR OF TOMOGRAM, AND COMPUTER-READABLE STORAGE MEDIUM AND APPARATUS THEREFOR

(71) Applicants: National Cerebral and Cardiovascular Center, Osaka (JP); NIHON MEDI-PHYSICS CO., LTD., Tokyo (JP)

(72) Inventors: Hidehiro Iida, Osaka (JP); Mayumi Nakazawa, Tokyo (JP)

(73) Assignees: Nihon Medi-Physics Co., Ltd., Tokyo (JP); National Cerebral and Cardiovascular Center, Osaka (JP)

( * ) Notice: Subject to any disclaimer, the term of this patent is extended or adjusted under 35 U.S.C. 154(b) by 278 days.

(21) Appl. No.: 13/888,080

(22) Filed: May 6, 2013

(65) Prior Publication Data

US 2013/0294671 A1    Nov. 7, 2013

(30) Foreign Application Priority Data

May 7, 2012   (EP) ..................................... 12167018
May 29, 2012  (JP) ................................. 2012-134231

(51) Int. Cl.
| G06K 9/00 | (2006.01) |
| G06T 11/00 | (2006.01) |
| G06T 7/00 | (2006.01) |
| A61B 6/00 | (2006.01) |
| A61B 6/03 | (2006.01) |

(52) U.S. Cl.
CPC ............. *G06T 11/003* (2013.01); *G06T 7/0083* (2013.01); *G06T 11/005* (2013.01); *A61B 6/037* (2013.01); *A61B 6/507* (2013.01); *G06T 2207/10081* (2013.01)

(58) Field of Classification Search
None
See application file for complete search history.

(56) References Cited

U.S. PATENT DOCUMENTS

| 4,718,010 A * | 1/1988 | Fujii .................................. 378/5 |
| 4,803,639 A * | 2/1989 | Steele et al. .................... 702/40 |
| 7,203,267 B2 * | 4/2007 | De Man et al. ................... 378/4 |
| 8,989,462 B2 * | 3/2015 | Fei et al. ....................... 382/128 |
| 2005/0105693 A1 * | 5/2005 | Zhao et al. ..................... 378/210 |
| 2006/0232608 A1 | 10/2006 | Riaz |
| 2008/0049891 A1 * | 2/2008 | Yin et al. ........................... 378/9 |
| 2010/0158194 A1 * | 6/2010 | Pack et al. .................. 378/98.12 |
| 2011/0103669 A1 * | 5/2011 | Michel et al. ................. 382/131 |

(Continued)

FOREIGN PATENT DOCUMENTS

WO    WO 2005/038491 A2    4/2005

OTHER PUBLICATIONS

European Patent Application No. 12167018.6: European Search report dated Sep. 27, 2012, 7 pages.

(Continued)

*Primary Examiner* — Jason Heidemann
(74) *Attorney, Agent, or Firm* — Baker & Hostetler LLP (57) ABSTRACT

Contour information is extracted from nuclear medicine projection data on a subject not subjected to a scattering correction and an absorption correction by performing a pixel value binarization processing based on a threshold scheme. If necessary, an interpolation processing is performed before reconstructing an image through an image reconstruction processing. Based on the reconstructed image, a second binarization processing is performed to generate a contour image.

20 Claims, 6 Drawing Sheets

(56) References Cited

U.S. PATENT DOCUMENTS

2012/0101368 A1* 4/2012 Masumoto .................. 600/420
2012/0294503 A1* 11/2012 Fei et al. ..................... 382/131

OTHER PUBLICATIONS

Iida et al, "Multicenter Evaluation of a Standardized Protocol for Rest and Acetazolamide Cerebral Blood Flow Assessment Using a Quantitative SPECT Reconstruction Program and Split-Dose 123I-Iodoamphetamine" The Journal of Nuclear Medicine, Oct. 2010, 51(10), 1624-1631.

Yoshiyuki Yamakawa et al, "Attenuation Correction using level set method for application specific PET scanners", Nuclear Science Symposium and Medical Imaging Conference, 2011, IEEE, p. 3130-3132, Oct. 23, 2011.

* cited by examiner

358° and 360°.

METHOD OF EXTRACTING CONTOUR OF TOMOGRAM, AND COMPUTER-READABLE STORAGE MEDIUM AND APPARATUS THEREFOR

This application is based on European patent application NO. 12167018 and Japanese patent application NO. 2012-134231, the content of which are incorporated hereinto by reference.

BACKGROUND

1. Technical Field

The present invention relates to an image processing method for a nuclear medicine image, such as tomograms of the positron emission tomography (abbreviated as PET hereinafter) and the single photon emission computed tomography (abbreviated as SPECT hereinafter), a program and an image processing apparatus for performing the method. More specifically, it relates to a contour extracting method for a tomogram, such as a PET image, a SPECT image and other nuclear medicine images, and a program and an image processing apparatus for performing the method.

2. Related Art

Nuclear medicine images, such as a PET image and a SPECT image, are useful for diagnosis of wide variety of diseases including cardiopathy and cancer. These images are obtained by administering a medicine labeled with a particular radioisotope (referred to as a radioactive medicine hereinafter) to a patient, detecting gamma rays emitted from the medicine with a dedicated camera, and reconstructing an image. The nuclear medicine image is superior to the other images used for diagnosis not only in disease specificity and sensitivity but also in availability of information on the function of the lesion.

As described above, the nuclear medicine image is obtained by detecting gamma rays emitted from the radioactive medicine administered to a subject. However, gamma rays attenuate and scatter in a living body, and therefore, the intensity of the detected gamma rays increases or decreases depending on the depth from the body surface. Therefore, in reconstructing the nuclear medicine image from the intensity of the detected gamma rays, the intensity has to be corrected by taking into account the attenuation and scattering of the gamma rays in the living body. This correction is particularly important when the nuclear medicine image is used for quantitative evaluation of a living body.

In many cases, an attenuation or absorption map (μ map) that represents a distribution of the absorption or attenuation coefficient (μ value) in a target region is used. More specifically, the attenuation correction is carried out by estimating a distribution of scattered radiations from the μ map, correcting projection data by taking into account the scattered radiations, and then reconstructing an image using the μ map (see Hidehiro Iida et al., "Multicenter Evaluation of a Standardized Protocol for Rest and Acetazolamide Cerebral Blood Flow Assessment Using a Quantitative SPECT Reconstruction Program and Split-Dose 123I-Iodoamphetamine.", J. Nucl. Med., (2010), vol. 51, No. 10, p. 1624-1631).

SUMMARY

To generate the μ map used for the correction described above, the contour of the subject needs to be extracted. In many cases, the contour extraction is performed according to a threshold scheme using nuclear medicine image data on the subject. In these cases, since the contour extraction is desirably performed using a high quality image, the nuclear medicine image used for contour extraction is typically subjected to an attenuation correction and a radiation scattering correction. In reconstructing the image used for contour extraction, a scattering and absorption correcting method that uses a μ map generated by elliptical approximation of the shape of the subject or a scattering and absorption correcting method that does not use any μ map has been used.

The method of extracting the contour of the subject from the reconstructed image according to the threshold scheme is the simplest method and therefore widely used at present. However, the conventional threshold-based contour extracting method that uses images subjected to the attenuation correction and the scattering correction may overestimate or underestimate the contour. Such an inaccurate extracted body contour is undesirable because it leads to inaccurate scattering correction and attenuation correction.

The present invention has been devised in view of such circumstances, and an object of the present invention is to provide an accurate contour extracting method using a nuclear medicine image of a subject, and a computer-readable storage medium and an apparatus for performing the method.

As a result of investigation, the inventor has found that, if a binarization processing based on a threshold scheme is performed on a projection data set that is not subjected to a radiation scattering correction, and an image is reconstructed from the data, an accurate contour image of a subject can be generated from nuclear medicine image data, and has completed the present invention.

In this specification, a projection data set refers to a set of projection images taken at different projection angles in one imaging process. For example, in the case where a patient is imaged in steps of 2° over 360°, the projection data set according to the definition in this specification is a set of 180 projection images taken at projection angles of 2°, 4°, 6°, … , 358° and 360°.

Furthermore, a sinogram refers to data that represents the projection images forming a projection data set arranged in the order of projection angle.

Furthermore, a collection angle range refers to a range of projection angles over which data is collected. For example, in the case where projection is performed in steps of 2° over a collection angle of 0° to 180°, the collection angle range is from 0° to 180°. In the case where the lower limit value of a collection angle range is 0°, and the upper limit value of the collection angle range is equal to or greater than 180°, the collection angle range will be denoted as a collection angle range of 0° to 180° or more.

A contour image forming method according to an aspect of the present invention is a method that generates a contour image from projection data on a subject without performing a scattering correction and an absorption correction, wherein a computer sequentially performs: a data acquisition step of acquiring a projection data set of nuclear medicine images collected over a collection angle range of 0° to 180° or more; a sinogram generation step of generating a sinogram from said acquired projection data set; a first binarization step of performing a first binarization processing on the generated sinogram; an image reconstruction step of reconstructing an image by back projection of said sinogram subjected to said first binarization processing; and a second binarization step of performing a second binarization processing on the reconstructed image.

A computer-readable storage medium according to another aspect of the present invention is a computer-readable storage medium storing a program that is installed in a computer to make the computer operate as a contour image generating apparatus that generates a contour image from projection data on a subject without performing a scattering correction and an absorption correction, wherein the program makes the computer sequentially perform: a data acquisition step of acquiring a projection data set of nuclear medicine images collected over a collection angle range of 0° to 180° or more; a sinogram generation step of generating a sinogram from said acquired projection data set; a first binarization step of performing a first binarization processing on the sinogram; an image reconstruction step of reconstructing an image by back projection of said sinogram subjected to the first binarization processing; and a second binarization step of performing a second binarization processing on the reconstructed image.

A contour image forming apparatus according to a further aspect of the present invention is a contour image forming apparatus that is designed to operate as a contour image generating apparatus that generates a contour image from projection data on a subject without performing a scattering correction and an absorption correction, comprising: a data acquiring section that has a function of acquiring a projection data set of nuclear medicine images; a sinogram generating section that generates a sinogram from the projection data set; a first binarization processing section that has a function of performing a binarization processing on the sinogram; an image reconstruction processing section that has a function of reconstructing an image by back projection of the sinogram; and a second binarization processing section that has a function of performing an image binarization processing on the reconstructed image.

The present invention is characteristically based on the finding that a contour can be accurately extracted according to a simple threshold scheme that uses projection data not subjected to a scattering correction and an absorption correction. As described above, since a high quality image is desirably used to determine the contour of an image, a common technique has been to extract the contour of a nuclear medicine image by using a tomogram subjected to a scattering correction and an absorption correction. However, as a result of investigation, the inventor has found that the radiation scattering correction can cause a change of the contour of the image to such an extent that the determined contour cannot accurately reproduce the image of the subject in some cases. And as a result of further investigation, the inventor has found that the contour can be accurately extracted even if the contour extraction according to the threshold scheme is performed on projection data not subjected to the radiation scattering correction and the absorption correction. Based on this finding, the inventor has finally completed the present invention.

In the contour image forming method, the contour image forming program and the contour image forming apparatus according to the present invention, the first binarization processing is a common binarization processing in which 0 is allocated to values equal to or smaller than a certain threshold, and a certain value (1, for example) is allocated to values greater than the threshold. For example, if the threshold is 25% of the maximum value, pixel values of pixels equal to or smaller than 25% of the maximum value are set at 0, and pixel values of pixels greater than 25% of the maximum value are set at 1.

The threshold used in the first binarization processing can be determined based on comparison between an image reconstructed using a projection data set subjected to a binarization processing and an image reconstructed without the binarization processing. The method of determining the threshold will be described later.

The image reconstruction performed in the image reconstruction step or by the image reconstructing section can be performed according to a common image reconstruction method in the field of nuclear medicine. According to the present invention, since the projection data set subjected to the binarization processing is used for the image reconstruction, pixels closer to the center of the image have greater pixel values in the resulting image. Thus, according to the present invention, the second binarization processing is performed on the reconstructed image to uniformalize the pixel values of the pixels inside the contour image. The threshold used in the second binarization processing can be any value that can uniformalize the pixel values of the pixels inside the contour without cutting out the data inside the contour. Typically, the threshold can be approximately 25% to 50% of the maximum value.

The contour image forming method according to the present invention may be configured to further comprise an interpolation step in which the computer perform a data interpolation of the sinogram subjected to the first binarization processing, and configured so that the image reconstruction step is to perform back projection using the sinogram subjected to the interpolation step. Similarly, the contour image forming program according to the present invention may be configured to further make the computer perform an interpolation step of performing a data interpolation of the sinogram subjected to the first binarization step, and configured so that the image reconstruction step is to perform back projection using the sinogram subjected to the interpolation step. Furthermore, the contour image forming apparatus according to the present invention may further comprise an interpolation processing section that has a function of performing a data interpolation of the sinogram.

With such a configuration, a contour image of higher quality in which the extracted contour is further smoothed can be obtained.

The interpolation processing in the interpolation step can be performed according to a common data interpolation method in the field of image processing. For example, a contour approximation method with a periodic function, such as a Fourier series approximation, or a quadratic or cubic spline interpolation can be used.

The interpolation processing section of the contour image forming apparatus can be any processing section that has a function of performing an interpolation processing such as those described above.

In the contour image forming method and the contour image forming program according to the present invention, the upper limit value of the collection angle range of the projection data set can be any value equal to or greater than 180°. However, the upper limit value is preferably equal to or greater than 360°, because the contour extraction accuracy is improved. From the viewpoint of data efficiency, the collection angle range is most preferably from 0° to 360°.

The contour image forming method according to the present invention may be configured so that the collection angle range of the projection data set acquired in the data acquisition step is from 0° to 360° or more (preferably from 0° to 360°), there is additionally performed an averaging step of calculating a sum, a geometric average or an arithmetic average of pixel values of each pixel in each piece of projection data forming the projection data set over a collection angle range of 0° to 180° and a corresponding pixel in projection data 180° opposite to the projection data and replacing pixel values in the projection data with the resulting values, and the sinogram generation step is performed using the projection data set subjected to the averaging step. In this case, the same calculation is performed for all the pixels included in the projection data set in the averaging step. For example, if the pixel value averaging processing of certain pixels is performed by calculating the geometric average thereof, the averaging processing of all the other pixels is also performed by calculating the geometric average thereof.

Similarly, the contour image forming program according to the present invention may be configured so that the collection angle range of the projection data set acquired in the data acquisition step is from 0° to 360° or more (preferably from 0° to 360°), the contour image forming program further makes the computer perform an averaging step of calculating a sum, a geometric average or an arithmetic average of pixel values of each pixel in each piece of projection data forming the projection data set over a collection angle range of 0° to 180° and a corresponding pixel in projection data 180° opposite to the projection data and replacing pixel values in the projection data with the resulting values, and the sinogram generation step is performed using the projection data set subjected to the averaging step. In this case also, of course, the same calculation is performed for all the pixels included in the projection data set in the averaging step.

Similarly, the contour image forming apparatus according to the present invention may be configured to further comprise a pixel value averaging section that has a function of calculating a sum, a geometric average or an arithmetic average of pixel values of each pixel in each piece of projection data forming the projection data set and a corresponding pixel in projection data 180° opposite to the projection data and replacing pixel values in the projection data with the resulting values. In this case also, as with the method and program described above, the averaging section performs the same calculation for all the pixels included in the projection data set.

With such configurations, the contour is made clearer, and thus the accuracy of the generated contour image is improved.

Alternatively, the averaging step described above may be performed for each piece of projection data after the projection data set is rearranged in the order of angle to form a sinogram.

Specifically, the contour image forming method according to the present invention may be configured so that the collection angle range of the projection data set acquired in the data acquisition step is from 0° to 360°, there is additionally performed an averaging step of calculating a sum, a geometric average or an arithmetic average of pixel values of each pixel in each piece of projection data forming the sinogram over a collection angle range of 0° to 180° and a corresponding pixel in projection data 180° opposite to the projection data and replacing pixel values in the projection data with the resulting values, and the first binarization step is performed using the sinogram subjected to the averaging step. In this case, the same calculation is performed for all the pixels included in the projection data set in the averaging step. For example, if the pixel value averaging processing of certain pixels is performed by calculating the geometric average thereof, the averaging processing of all the other pixels is also performed by calculating the geometric average thereof.

Similarly, the contour image forming program according to the present invention may be configured so that the collection angle range of the projection data set acquired in the data acquisition step is from 0° to 360°, the contour image forming program further makes the computer perform an averaging step of calculating a sum, a geometric average or an arithmetic average of pixel values of each pixel in each piece of projection data forming the sinogram over a collection angle range of 0° to 180° and a corresponding pixel in projection data 180° opposite to the projection data and replacing pixel values in the projection data with the resulting values, and the first binarization step is performed using the sinogram subjected to the averaging step. In this case also, of course, the same calculation is performed for all the pixels included in the projection data set in the averaging step.

Similarly, the contour image forming apparatus according to the present invention may be configured to further comprise a pixel value averaging section that has a function of calculating a sum, a geometric average or an arithmetic average of pixel values of each pixel in each piece of projection data forming the sinogram and a corresponding pixel in projection data 180° opposite to the projection data and replacing pixel values in the projection data with the resulting values. In this case also, as with the method and the program described above, the averaging section performs the same calculation for all the pixels included in the projection data set.

The present invention enables a high quality contour image to be generated from projection data on a subject.

BRIEF DESCRIPTION OF THE DRAWINGS

The above and other objects, advantages and features of the present invention will be more apparent from the following description of certain preferred embodiments taken in conjunction with the accompanying drawing.

DETAILED DESCRIPTION

The invention will be now described herein with reference to illustrative embodiments. Those skilled in the art will recognize that many alternative embodiments can be accomplished using the teachings of the present invention and that the invention is not limited to the embodiments illustrated for explanatory purposed.

In the following, the present invention will be described with reference to the drawings. In all the drawings, similar components are denoted by similar reference numerals and symbols, thus avoiding duplication of the explanation as appropriate. The examples described below are merely intended to illustrate preferred embodiments of the present invention and do not limit the scope of the present invention in any sense.

Figure 1:
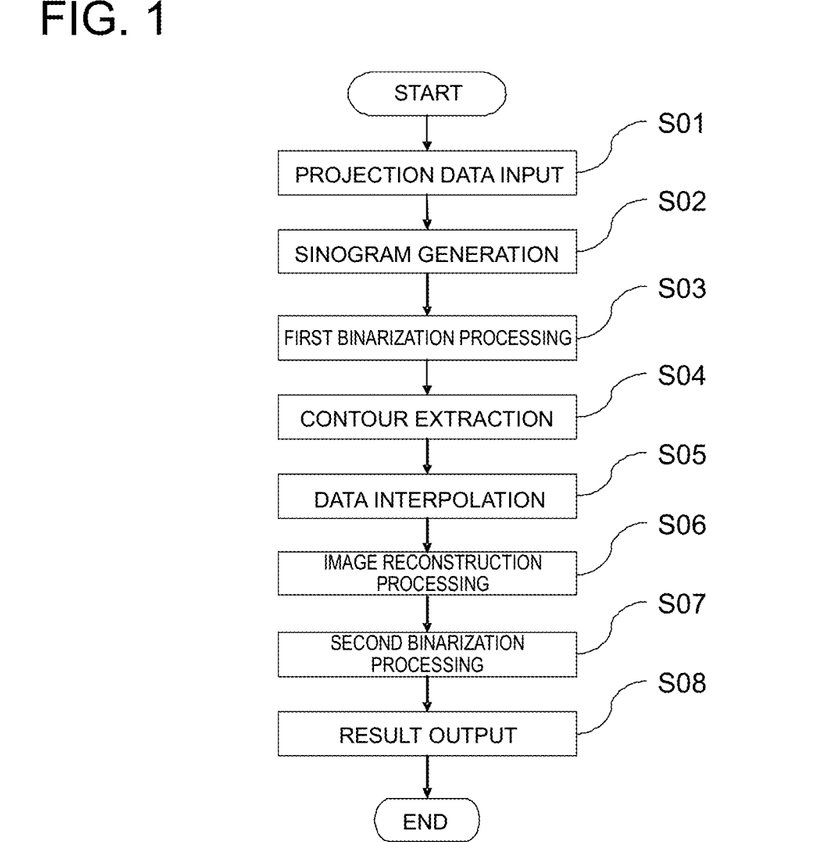
FIG. 1 is a flowchart schematically showing a process performed by a contour image forming apparatus according to a preferred embodiment of the present invention.
Figure 2:
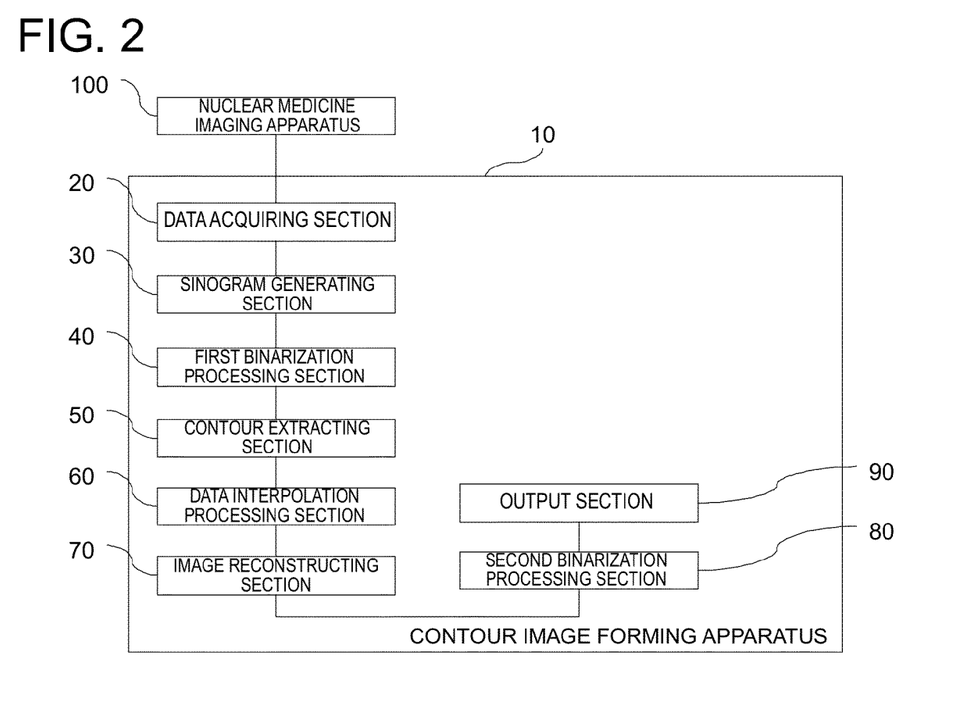
FIG. 2 is a functional block diagram showing a contour image forming apparatus according to the preferred embodiment of the present invention.

FIG. 1 is a flowchart schematically showing a process performed by a contour image forming apparatus according to a preferred embodiment of the present invention, and FIG. 2 is a functional block diagram showing the contour image forming apparatus according to the preferred embodiment of the present invention. A contour image forming apparatus 10 according to the present invention can be a computer with a contour image forming program 300 installed therein, and a contour image forming method according to the present invention can be implemented by operating the contour image forming apparatus 10.

According to the preferred embodiment, the contour image forming apparatus 10 comprises a data acquiring section 20, a sinogram generating section 30, a first binarization processing section 40, a contour extracting section 50, a data interpolation processing section 60, an image reconstructing section 70, a second binarization processing section 80, and an output section 90. According to the preferred embodiment, the contour image forming apparatus 10 is connected to a nuclear medicine imaging apparatus 100, such as a SPECT apparatus, by a telecommunication line.

Figure 3:
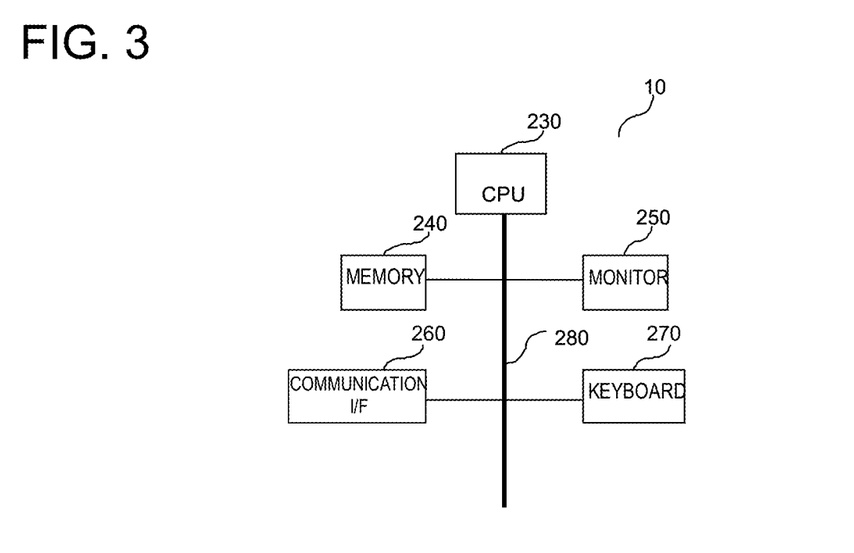
FIG. 3 is a diagram showing a system configuration of the contour image forming apparatus according to the preferred embodiment of the present invention.

FIG. 3 shows a system configuration of the contour image forming apparatus 10 according to the most preferred embodiment of the present invention. According to the preferred embodiment, the contour image forming apparatus 10 comprises a CPU 230, a memory 240, an output device 250, such as a monitor, a communication interface 260, and an input device 270, such as a keyboard, which are interconnected by a bus 280. The cerebral blood flow quantitation apparatus 10 may additionally comprise a CD-ROM drive, a USB interface or the like. The communication interface 260 is used to connect the contour image forming apparatus 10 to the nuclear medicine imaging apparatus 100. The memory 240 stores the contour image forming program 300 according to the present invention.

The contour image forming apparatus 10 according to the present invention first performs a data acquisition step in the data acquiring section 20, in which a projection data set for a nuclear medicine image to be processed is input to the computer system (Step S01). To obtain necessary information to extract a contour, the collection angle range of the projection data set is from 0° to 180° or more, more preferably from 0° to 360° or more, or most preferably from 0° to 360°.

The projection data set may be obtained by imaging with a common nuclear medicine imaging apparatus, such as a SPECT apparatus and a PET apparatus. The projection data set is directly loaded from the nuclear medicine imaging apparatus 100 into the contour image forming apparatus 10 via a network in a computer-readable format, such as the DICOM format. Alternatively, the projection data set may be stored in a computer-readable storage medium, such as a hard disk, a CD-ROM and a DVD, and loaded from the storage medium into the computer system by means of a reader incorporated in the computer system.

Next, the contour image forming apparatus 10 performs a sinogram generation step in the sinogram generating section 30, in which a sinogram is generated from the projection data set (Step S02). The sinogram is two-dimensional data composed of pieces of projection data from one cross section arranged in the order of projection angle and can be generated in a well-known method. For example, consider a case where projection data (x, y) are obtained every 4° over an angle range of 0° to 360° (that is, the projection angle ranges from 0° to 360°). In this case, a sinogram for any cross-sectional plane (y) can be generated by obtaining projection data (x) at a y value (that is, at a site in the direction of the body axis) over an angle range of 0° to 360°, and arranging the projection data (x) at the respective angles one by one from top to bottom in a two-dimensional coordinate system.

Once the sinogram generation step is completed, the contour image forming apparatus 10 performs a first binarization processing step in the first binarization processing section 40 (Step S03). The binarization processing in this case can be a common binarization processing in which pixel values equal to or lower than a preset threshold are replaced by 0, and pixel values greater than the threshold are replaced by 1, for example.

Figure 4:
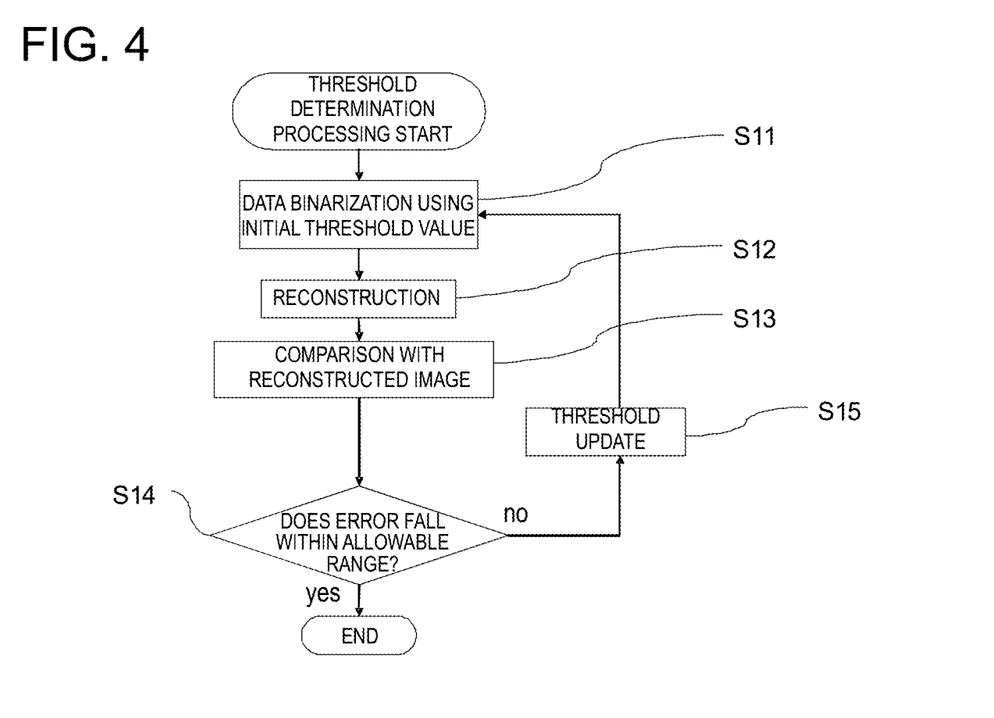
FIG. 4 is a flowchart showing a process flow of a preferred example of a method of determining a threshold used for a first binarization processing.

The threshold used in the first binarization processing step can be independently determined based on comparison with a reconstructed image. FIG. 4 is a flowchart showing a threshold determining method used in the first binarization processing step in the preferred embodiment. In determining the threshold, the binarization processing is first performed with a certain initial value (Step S11), and then, an image is reconstructed by a back projection processing (Step S12). The initial value of the threshold can be any value empirically determined by the user. Typically, 25% or so of the maximum of the pixel values can be used as the initial value.

Once the image reconstruction processing is completed, the reconstructed image is compared with another reconstructed image of the subject separately prepared (step S13), and it is determined whether the shape error between the images falls within an allowable range or not (step S14). The reconstructed images used in these steps are generated from the projection data set used in this process in a well-known image reconstruction method that involves no scattering or absorption correction. The image reconstruction method used in this case may be a filtered back projection method, for example. The shape error can be determined by visual check of the images superimposed one on the other by the user. Alternatively, of course, a value indicative of the error, such as the residual sum of squares, may be calculated and compared with an allowable value thereof. Then, if it is determined that the error is greater than the allowable range (if no in Step S14), the threshold is changed (Step S15), and the process from Steps S11 to S14 is repeated. If it is determined that the error falls within the allowable range (if yes in Step S14), the threshold is adopted as the threshold used for the process.

Returning to FIG. 1, the process performed by the contour image forming apparatus 10 will be described. When the first binarization processing step is completed, the contour extracting section 50 performs a contour extracting step, in which contour data is extracted from the sinogram (Step S04). According to the preferred embodiment, in the contour extracting step, a differential processing can be performed on the projection data subjected to the binarization processing to extract a first peak position from each of the left and right ends of each coordinate axis. The differential processing can be performed by applying a well-known differential filter, such as a Sobel filter and a Prewitt filter, on the sinogram generated from the projection data set. Two pieces of contour data are extracted on the left and right sides of the sinogram by this processing.

Once the contour extracting step is completed, the data interpolation processing section 60 performs an interpolation processing by performing an interpolation step on the left and right contour data (Step S05). In this interpolation processing, a well-known method can be used, such as a contour approximation method with a periodic function, such as a Fourier series approximation, and a quadratic or cubic spline interpolation. This processing converts the extracted contour data into smooth data.

Once the interpolation step is completed, a certain pixel value (1, for example) is allocated to the pixels in the region between the two, left and right pieces of contour data, and then, the image reconstructing section 70 performs an image reconstruction step to generate a reconstructed image by back projection of the sinogram (Step S06). In the reconstructed image formed in this step, pixels closer to the center of the image have greater pixel values. Then, the second binarization processing performs a second binarization step to uniformalize the pixel values in the contour image (Step S07). The threshold used in the second binarization step can have any magnitude that does not cause a loss of contour image data and can be determined by comparison between the images before and after the binarization processing.

Once the second binarization processing is completed, the output section 90 outputs the contour image to the output device, such as a display (Step S08). The contour image can be formed by the series of processings described above.

The contour image forming apparatus 10 according to the present invention may further comprise a pixel value averaging section (not shown) that has a function of calculating the sum, the geometric average or the arithmetic average of pixel values of each pixel in each piece of projection data forming the projection data set and a corresponding pixel in projection data 180° opposite to the projection data, and replacing the pixel values in the projection data with the resulting values. In this case, a pixel value averaging step (not shown) is performed on the projection data set acquired in the data acquisition step (Step S01), and the sinogram is generated in the sinogram generation step (Step S02) using the projection data set subjected to the pixel value averaging step. With such a configuration, in the projection data set subjected to the averaging processing, fluctuations of the contour are smoothed, and the contour is made clearer. Therefore, the accuracy of the generated contour image can be improved. Alternatively, the pixel value averaging step described above may be performed using each piece of projection data forming a projection data set in the form of a sinogram.

The pixel value averaging section is implemented by loading a contour image forming program incorporating a pixel value averaging module (not shown) described later into the computer.

Figure 5:
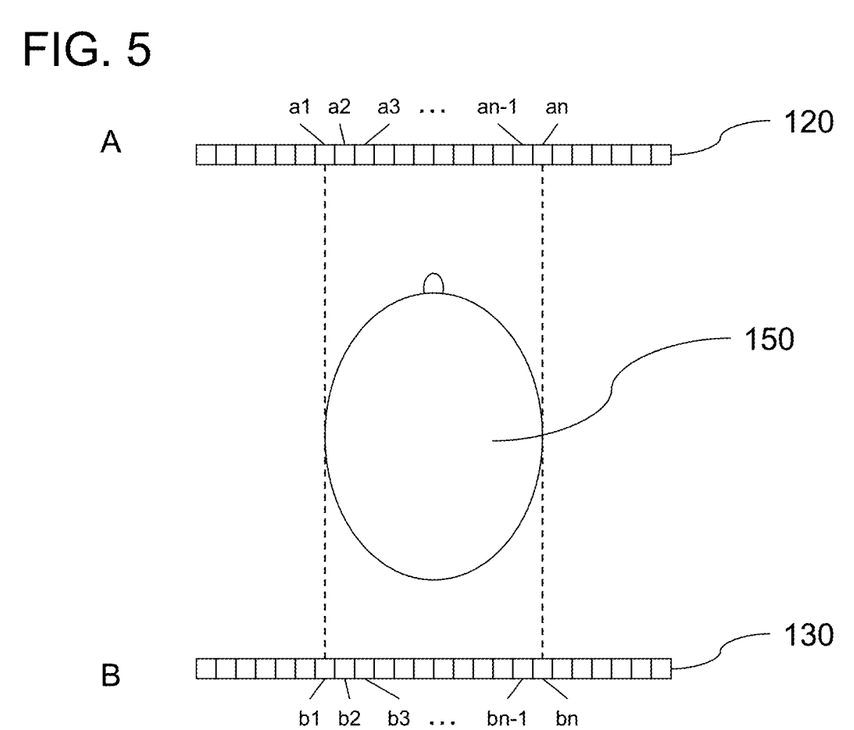
FIG. 5 is a schematic diagram for illustrating a pixel value averaging processing for nuclear medicine image data for a head.

FIG. 5 schematically shows an example of the pixel value averaging step performed on a nuclear medicine image of a head. In FIG. 5, a projection image A and a projection image B are 180° opposite to each other. In this case, the sum, the geometric average or the arithmetic average of pixel values is calculated for each pair of corresponding pixels in the projection images A and B, such as pairs of pixels a1 and b1, pixels a2 and b2, pixels a3 and b3, ..., pixels an−1 and bn−1, pixels an and bn and so on. Then, the pixel values of the pixels a1, a2, a3, ..., an−1, an and so on of the projection image A are replaced with the values calculated for the respective pixels. This processing is performed over a projection angle of 0° to 180° to complete the averaging step. Of course, the same kind of calculation is performed for all the pixels included in the projection data set in the averaging step. For example, if the pixel value averaging processing of the pixels a1 and b1 is performed by calculating the geometric average thereof, the averaging processing of the other pixels, such as the pixels a2 and b2, is also performed by calculating the geometric average thereof.

This is the end of the description of the configuration and operation of the contour image forming apparatus 10 according to a preferred embodiment of the present invention.

Next, the contour image forming program 300 according to the present invention will be described. As described above, the contour image forming apparatus 10 according to the present invention can be a computer with the contour image forming program 300 installed therein.

Figure 6:
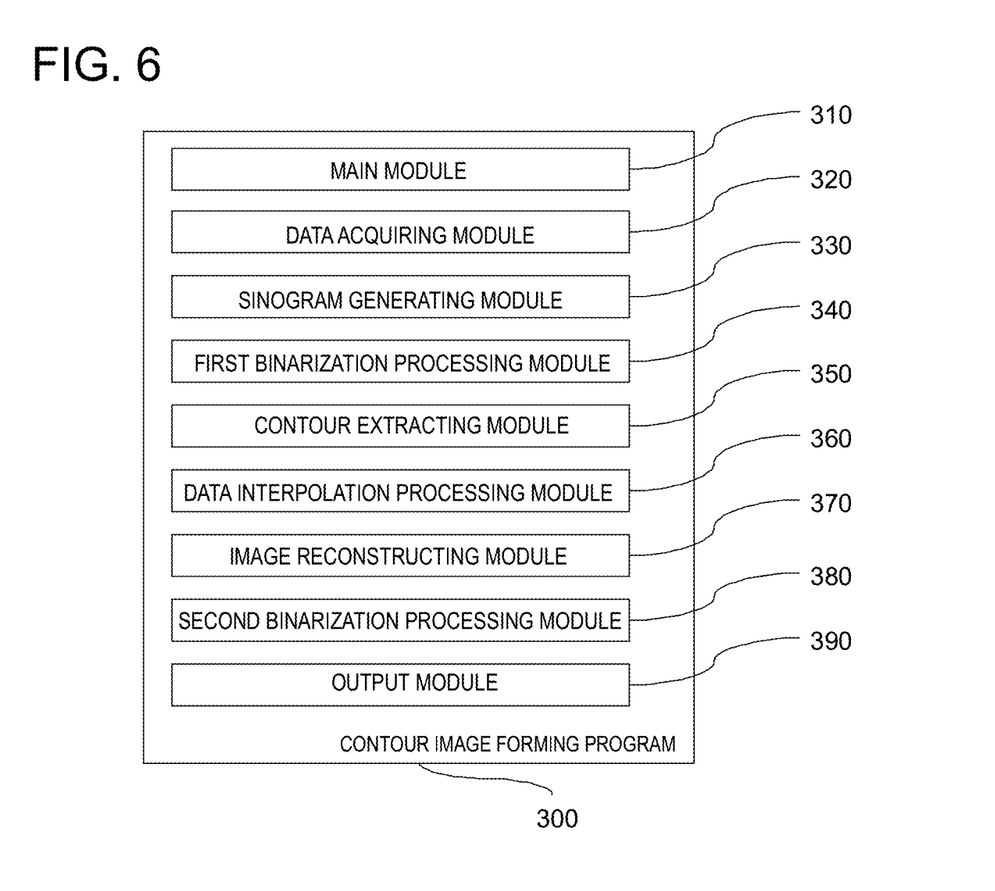
FIG. 6 is a diagram showing a configuration of a contour image forming program according to a preferred embodiment of the present invention.

FIG. 6 shows a configuration of the contour image forming program 300 according to a preferred embodiment of the present invention. According to the preferred embodiment, the contour image forming program 300 comprises a main module 310 that controls the processings, a data acquiring module 320, a sinogram generating module 330, a first binarization processing module 340, a contour extracting module 350, a data interpolation processing module 360, an image reconstructing module 370, a second binarization processing module 380, and an output module 390.

The data acquiring module 320 makes the computer perform the processing of Step S01.

The sinogram generating module 330 makes the computer perform the processing of Step S02.

The first binarization processing module 340 makes the computer perform the processing of Step S03.

The contour extracting module 350 makes the computer perform the processing of Step S04.

The data interpolation processing module 360 makes the computer perform the processing of Step S05.

The image reconstructing module 370 makes the computer perform the processing of Step S06.

The second binarization processing module 380 makes the computer perform the processing of Step S07.

The output module 390 makes the computer perform the processing of Step S08.

The contour image forming program 300 may further comprise a pixel value averaging module (not shown). The pixel value averaging module loaded into the computer makes the computer function as the pixel value averaging section described above and perform the pixel value averaging step.

The contour image obtained by implementing the present invention can be suitably used for forming a $\mu$ map. For example, a $\mu$ map can be easily formed by replacing the pixel values other than 0 in the contour image obtained by implementing the present invention with an arbitrary absorption coefficient. The contour image obtained by implementing the present invention accurately traces the contour of the subject image, and therefore, the $\mu$ map formed by using the contour image allows scattering correction and absorption correction to be performed with higher precision.

EXAMPLE

A projection data set for SPECT of a head administered with I-1231 MP (available from Nihon Medi-Physics Co., Ltd.) was used (the projection angle pitch was 4°, the number of slices of projection data was 90, and the projection angle range was 0° to 360°). The projection data set was in the form of a so-called sinogram, in which projection images taken at the respective projection angles and represented in the horizontal direction are arranged in the vertical direction in the order of projection angle.

Figure 7A:
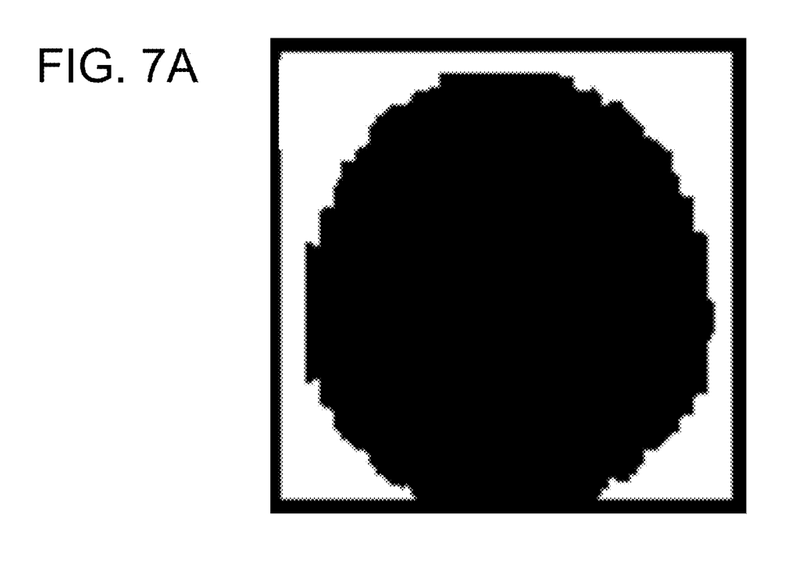
FIG. 7A shows an example of a contour image of a head obtained by a method according to the present invention.
Figure 7B:
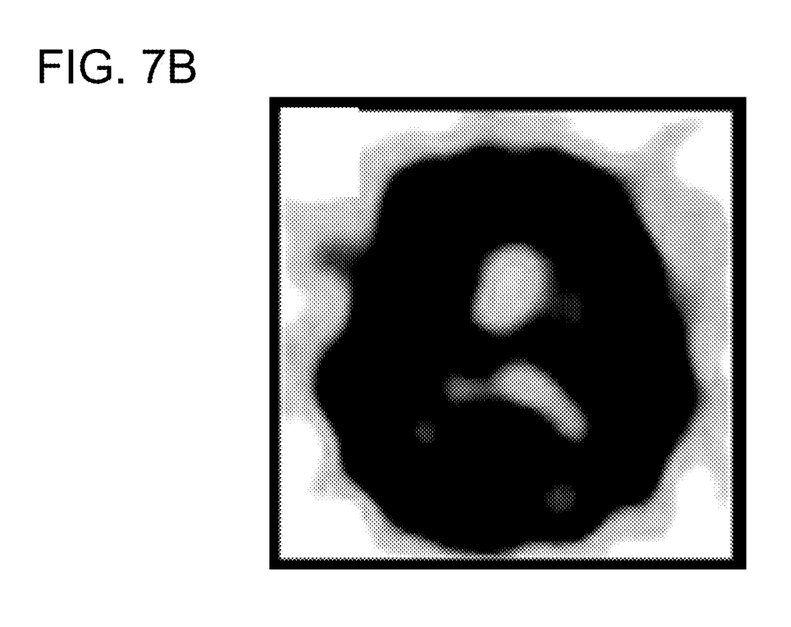
FIG. 7B shows a reconstructed image obtained from a projection data set used for generating the contour image (a filtered back projection method is used).

The projection data set described above was subjected to the first binarization processing by using 25% of the maximum of the pixel values as the threshold. Then, the projection data set subjected to the binarization was used to perform 360° back projection, thereby reconstructing an image. Then, the reconstructed image was subjected to the second binarization processing by using 50% of the maximum of the pixel values as the threshold to generate a contour image (FIG. 7A). The generated contour image successfully reproduced the contour of the reconstructed image (FIG. 7B) obtained from the projection data set. From this result, it is confirmed that the contour image can be accurately reproduced by the method according to the present invention.

It is apparent that the present invention is not limited to the above embodiment, and may be modified and changed without departing from the scope and spirit of the invention.

What is claimed is:

1. A computer-implemented contour image forming method that generates a contour image from projection data on a subject, comprising:
   acquiring a projection data set of nuclear medicine images collected over a collection angle range of 0° to 180° or more;
   generating a sinogram from said acquired projection data set that is uncorrected for scatter;
   performing a first binarization processing on the generated sinogram;
   reconstructing an image by back projection of said sinogram subjected to said first binarization processing; and
   performing a second binarization processing on the reconstructed image to generate the contour image.

2. The contour image forming method according to claim 1, further comprising:
   performing a data interpolation of the sinogram after performing the first binarization processing on the generated sinogram; and
   wherein the reconstructing an image by back projection is performed after performing the data interpolation of the sinogram.

3. The contour image forming method according to claim 1, wherein an upper limit value of the collection angle range of the projection data set is equal to or greater than 360°.

4. The contour image forming method according to claim 3, comprising:
   after acquiring a projection data set of nuclear medicine images and before generating a sinogram from said acquired projection data set, calculating at least one of a sum, a geometric average or an arithmetic average of pixel values of each pixel in a set of pixels in the projection data forming the projection data set over a collection angle range of 0° to 180° and a corresponding pixel in projection data 180° opposite to the projection data; and
   replacing pixel values in the set of pixels with the calculated pixel values.

5. The contour image forming method according to claim 4, further comprising performing the same of at least one of a sum, a geometric average or an arithmetic average of pixel values for each pixel in the set of pixels included in the projection data.

6. The contour image forming method according to claim 3, comprising:
   after generating a sinogram and before performing a first binarization processing calculating at least one of a sum, a geometric average or an arithmetic average of pixel values of each pixel in a set of pixels in the projection data forming the sinogram over a collection angle range of 0° to 180° and a corresponding pixel in projection data 180° opposite to the projection data and replace pixel values in the projection data with the calculated pixel values.

7. The contour image forming method according to claim 6, comprising: performing the same of at least one of a sum, a geometric average or an arithmetic average of pixel values for each pixel in the set of pixels included in the projection data.

8. A non-transitory computer-readable storage medium storing computer instructions for generating a contour image from projection data on a subject, the computer instructions, upon execution on a computing device, at least cause the computing device to:
   acquire a projection data set of nuclear medicine images collected over a collection angle range of 0° to 180° or more;
   generate a sinogram from said acquired projection data set that is uncorrected for scatter;
   perform a first binarization process on said sinogram;
   reconstruct an image by back projection of said sinogram subjected to the first binarization process; and
   perform a second binarization process on the reconstructed image to generate the contour image.

9. The computer-readable storage medium according to claim 8, wherein computer instructions for generating a contour image further at least cause the computing device to interpolate the sinogram subjected after the computing device is cause to perform a first binarization process on said sinogram and before the computing device is caused to reconstruct an image by back projection of said sinogram.

10. The computer-readable storage medium according to claim 8, wherein an upper limit value of the collection angle range of the projection data set is equal to or greater than 360°.

11. The computer-readable storage medium according to claim 10, wherein computer instructions for generating a contour image further at least cause the computing device to calculate, after causing the computing device to acquire a projection data set before causing the computing device to generate a sinogram from said acquired projection data set, calculate at least one of a sum, a geometric average or an arithmetic average of pixel values of each pixel in a set of pixels in the projection data forming the projection data set over a collection angle range of 0° to 180° and a corresponding pixel in projection data 180° opposite to the projection data and replace pixel values in the projection data with the calculated pixel values.

12. The computer-readable storage medium according to claim 11, wherein computer instructions for generating a contour image further at least cause the computing device to perform the same of at least one of a sum, a geometric average or an arithmetic average for all of the pixels included in the projection data set.

13. The computer-readable storage medium according to claim 10, wherein computer instructions for generating a contour image further at least cause the computing device to calculate, after instructions for causing the computing device to generate a sinogram and before causing the computing device to perform a first binarization processing, at least one of a sum, a geometric average or an arithmetic average of pixel values of each pixel in a set of pixels in the projection data forming the sinogram over a collection angle range of 0° to 180° and a corresponding pixel in projection data 180° opposite to the projection data and replace pixel values in the projection data with the calculated pixel values.

14. The computer-readable storage medium according to claim 13, wherein computer instructions for generating a contour image further at least cause the computing device to perform the same of at least one of a sum, a geometric average or an arithmetic average of pixel values for each pixel in the set of pixels included in the projection data.

15. A contour image forming apparatus configured to generate a contour image from projection data on a subject, comprising:
   at least one processor configured to acquire a projection data set of nuclear medicine images;

at least one processor configured to generate a sinogram from the projection data set that is uncorrected for scatter;

at least one processor configured to perform a binarization processing on the sinogram;

at least one processor configured to reconstruct an image by back projection of the sinogram; and at least one processor configured to perform an image binarization processing on the reconstructed image to generate the contour image.

16. The contour image forming apparatus according to claim 15, further comprising:

at least one processor configures to perform a data interpolation of the sinogram.

17. The contour image forming apparatus according to claim 15, further comprising:

at least one processor configured to calculate at least one of a sum, a geometric average or an arithmetic average of pixel values of each pixel in a set of pixels in the projection data forming the projection data set or the sinogram and a corresponding pixel in projection data 180° opposite to the projection data: and at least one processor configured to replace pixel values in the projection data with the calculated pixel values.

18. The contour image forming apparatus according to claim 17, wherein the at least one processor configured to calculate, is further configured to perform the same of at least one of a sum, a geometric average or an arithmetic average for all of the pixels included in the set of pixels in the projection data set.

19. The contour image forming apparatus according to claim 18, wherein the at least one processor is further configured to calculate after generating the sinogram and before performing the binarization processing.

20. The contour image forming apparatus according to claim 18, wherein the at least one processor is further configured to calculate before generating the sinogram.

* * * * *